United States Patent [19]

Shiono et al.

[11] Patent Number: 4,694,090
[45] Date of Patent: Sep. 15, 1987

[54] CHROMAN COMPOUNDS USEFUL AS ANALGERICS AND ANTIOXIDANTS

[75] Inventors: Manzo Shiono; Yoshiji Fujita; Takashi Nishida, all of Kurashiki, Japan

[73] Assignee: Kuraray Co., Ltd., Kurashiki, Japan

[21] Appl. No.: 679,455

[22] Filed: Dec. 7, 1984

[51] Int. Cl.$^4$ ............................................. C07D 311/72
[52] U.S. Cl. ...................................... 549/407; 549/389
[58] Field of Search ................................ 549/407, 389

[56] References Cited

U.S. PATENT DOCUMENTS

| 4,374,258 | 2/1983 | Horner et al. | 549/407 |
| 4,404,304 | 9/1985 | Horner et al. | 549/407 |
| 4,511,685 | 4/1985 | Nissen et al. | 549/407 |

Primary Examiner—Nicky Chan
Attorney, Agent, or Firm—Burns, Doane, Swecker & Mathis

[57] ABSTRACT

Novel chroman compounds which have excellent antioxidant activity and/or analgesic activity or serve as precursors for such active compounds are provided. There are also provided uses of these active compounds as an antioxidant and/or analgesic.

13 Claims, No Drawings

CHROMAN COMPOUNDS USEFUL AS ANALGERICS AND ANTIOXIDANTS

BACKGROUND OF THE INVENTION

1. Field of the Invention

This invention relates to novel chroman compounds, and to uses of these compounds as antioxidants or analgesics or precursors for the compounds having antioxidant activity and/or analgesic activity.

2. Description of the Prior Art

Recently, vitamin E has become a focus of attention as a highly safe antioxidant. However, it is relatively expensive and moreover liable to be oxidized and discolor, and therefore it has not been commonly employed as an antioxidant yet.

And it is known that compounds having a chroman skeleton such as 2-(N,N-dimethylamino)ethyl 2-(2,2,5,7,8-pentamethyl-6-chromanyloxy)isobutyrate, 2-(2,2,5,7,8-pentamethyl-6-chromanyloxy)isobutyl nicotinate, etc. have cholesterol lowering activity [Japanese Laid-Open Patent Publication No. 94382/1980].

An object of the invention is to provide novel chroman compounds which are either superior in antioxidant activity to vitamin E or useful as precursors of such antioxidant-active compounds.

Another object of the invention is to provide novel chroman compounds which are either analgesic-active or useful as precursors for such analgesic-active compounds.

A further object of the invention is to provide uses of the antioxidant-active chroman compounds as an antioxidant.

A further object of the invention is to provide uses of the analgesic-active chroman compounds as an analgesic.

These objects as well as other objects and advantages of the invention will become apparent to those skilled in the art from the following detailed description.

SUMMARY OF THE INVENTION

In accordance with this invention, there are provided a compound of general formula (I)

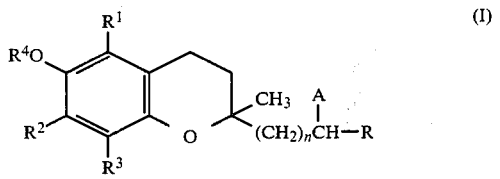

Wherein A is an amino or hydroxyl group, R is a hydrogen atom or a hydroxymethyl or carboxyl group when A is an amino group, or a carboxyl group when A is a hydroxyl group, $R^1$ is a hydrogen atom or a lower alkyl group, $R^2$ and $R^3$ are the same or different and each is a hydrogen atom or a lower alkyl or alkoxy group or $R^2$ and $R^3$ combinedly represent a —CH=CH—CH=CH— group, $R^4$ is a hydrogen atom or a protective group and n is an integer of 0-2, inclusive of the ester and/or salt form thereof [hereinafter collectively referred to as "chroman compounds (I)"].

And in accordance with this invention, there are provided uses of a compound of general formula (I-1)

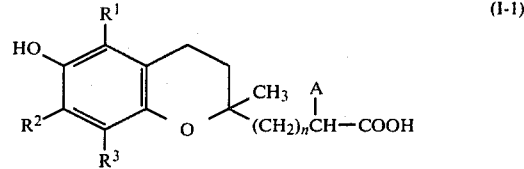

wherein A, $R^1$, $R^2$, $R^3$ and n are as defined above relative to general formula (I), inclusive of the ester and/or salt form thereof [hereinafter collectively referred to as "chroman compounds (I-1)] as an antioxidant.

Further in accordance with this invention, there is also provided a pharmaceutical composition for analgesic, said composition being composed of (1) an amount, effective for analgesic, of a compound of general formula (I-2)

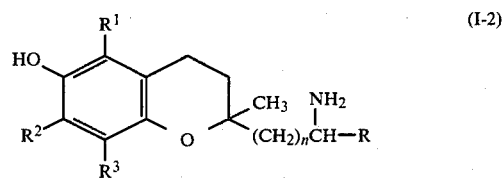

wherein R, $R^1$, $R^2$, $R^3$ and n are as defined above relative to general formula (I), inclusive of the pharmaceutically acceptable ester and/or salt form thereof [hereinafter collectively referred to as "chroman compounds (I-2)], and (2) a pharmaceutically acceptable diluent or carrier.

DETAILED DESCRIPTION OF THE INVENTION

Referring to the above general formula (I), A is an amino or hydroxyl group. R is a hydrogen atom or a hydroxymethyl or carboxyl group when A is an amino group, or a carboxyl group when A is a hydroxyl group. $R^1$ is a hydrogen atom or a lower alkyl group such as methyl, ethyl, propyl, butyl, etc. $R^2$ and $R^3$ are the same or different and each is a hydrogen atom, a lower alkyl group such as methyl, ethyl, propyl, butyl, etc., or a lower alkoxy group such as methoxy, ethoxy, propoxy, butoxy, etc., or $R^2$ and $R^3$ combinedly form a —CH=CH—CH=CH— group. $R^4$ is a hydrogen atom or a protective group. Said protective group may be any of conventional protective groups if only protection of hydroxyl group can be attained, and may be exemplified by carboxWnylic acyl groups (e.g. acetyl, propionyl, butyryl, benzoyl, etc.), alkyl group having 1 to 4 carbon atoms, such as methyl and tert-butyl, triphenylmethyl, benzyl, trimethylsilyl and so on. n is an integer of 0-2.

The compound of general formula (I) may be grouped, according to the substituents A and R, into the following four classes:

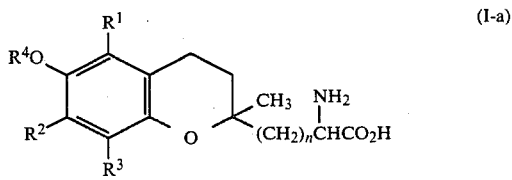

-continued

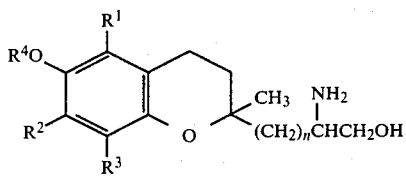
(I-b)

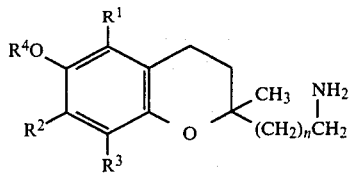
(I-c)

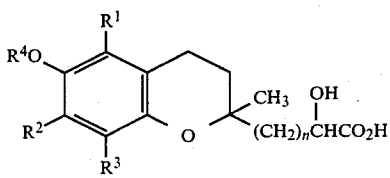
(I-d)

The esters and salts of the α-amino acid of general formula (I-a) include such ester form as an alkyl ester, e.g. methyl ester, ethyl ester, propyl ester, butyl ester, octyl ester, tetradecyl ester, stearyl ester, etc.; and such salt form as an alkali metal salt, e.g. lithium salt, sodium salt, potassium salt, etc., or a mineral acid salt, e.g. hydrochloride, sulfate, nitrate, etc. or an organic sulfonic acid salt, e.g. p-toluenesulfonate, methanesulfonate, etc. The esters and salts of the α-hydroxycarboxylic acid of general formula (I-d) include such ester form as an alkyl ester, e.g. methyl ester, ethyl ester, propyl ester, butyl ester, octyl ester, tetradecyl ester, stearyl ester, etc.; and such salt form as an alkali metal salt, e.g. lithium salt, sodium salt, potassium salt, etc., or an alkaline earth metal salt, e.g. magnesium salt, calcium salt, etc., or an optionally lower alkyl-substituted ammonium salt, e.g. ammonium salt, methylammonium salt, ethylammonium salt, trimethylammonium salt, tetramethylammonium salt, tetraethylammonium salt, etc.

The α-amino acid of general formula (I-a) can be produced by reacting an aldehyde of general formula

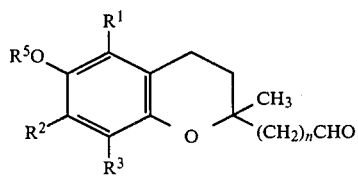
(II)

wherein $R^1$, $R^2$, $R^3$ and n each have the same meanings as in general formula (I), and $R^5$ is the same as or different from $R^4$ in general formula (I) and represents a hydrogen atom or a protective group, with ammonium carbonate and an alkali metal cyanide and then hydrolyzing the thus-obtained hydantoin of general formula

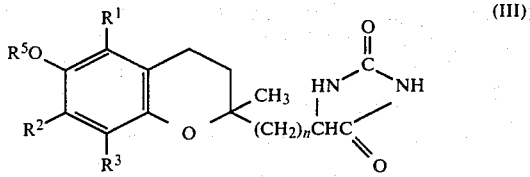
(III)

wherein $R^1$, $R^2$, $R^3$, $R^5$ and n each have the same meanings as in general formula (II). Said alkali metal cyanide is, for example, sodium cyanide, potassium cyanide, lithium cyanide, etc. The reaction of the aldehyde of general formula (II) with ammonium carbonate and the alkali metal cyanide can be carried out under conditions which are generally known to be adequate for hydantoin syntheses. Thus, for instance, the aldehyde of general formula (II), about 1–10 moles, preferably about 1–3 moles, per mode of aldehyde, of ammonium carbonate and about 1–10 moles, preferably about 1–3 moles, per mole of aldehyde, of the alkali metal cyanide are reacted in a solvent such as water, methanol, ethanol, tetrahydrofuran, etc. at a temperature between room temperature and 100° C., preferably in the range of 40°–60° C. The reaction mixture is then concentrated, a small amount of concentrated hydrochloric acid is added to the concentrate, and the mixture is heated at about 80°–100° C. for about 1–10 minutes, whereby the hydantoin of general formula (III) is obtained. Hydrolysis of the thus-obtained hydantoin by the conventional method gives the α-amino acid of general formula (I-a). The hydrolysis is carried out, for example, by reacting the hydantoin and about 1–5 moles, per mole of hydantoin, of an alkali metal hydroxide such as sodium hydroxide, potassium hydroxide, etc. in an aqueous medium at a temperature of 80°–150° C., preferably 100°–130° C., followed by neutralization of the alkali being in the system with a mineral acid such as hydrochloric acid, sulfuric acid, etc.

When subjected to the generally known esterification and/or salt formation reaction, the α-amino acid of general formula (I-a) is converted to an ester or salt of said α-amino acid or a salt of said α-amino acid ester. Thus, for example, reacting the α-amino acid of general formula (I-a) with an alkyl alcohol such as methyl alcohol, ethyl alcohol, propyl alcohol, butyl alcohol, octyl alcohol, stearyl alcohol, etc. in the presence of hydrogen chloride, sulfuric acid, thionyl chloride or the like in an amount at least equivalent to said α-amino acid at about $-20°$ C. to $+40°$ C., followed by neutralization of the reaction mixture, for example, with an aqueous sodium bicarbonate, etc. gives the corresponding α-amino acid ester. The α-amino acid of general formula (I-a) or an ester thereof is converted to the corresponding salt by dissolving said α-amino acid or ester thereof in water, methyl alcohol, ethyl alcohol, propyl alcohol, tetrahydrofuran, diethyl ether or the like and then adding to the solution an approximately equivalent amount, to the α-amino acid or ester thereof, of a mineral acid such as hydrogen chloride, sulfuric acid, nitric acid, etc., or an organic sulfonic acid such as p-toluenesulfonic acid, methanesulfonic acid, etc., or an alkali metal hydroxide such as lithium hydroxide, sodium hydroxide, potassium hydroxide, etc.

The α-amino acid of general formula (I-a) or an ester thereof, inclusive of salt form, produced in the above manner can be separated and recovered by any of the methods generally known for the separation and recovery of amino acids and esters thereof, and salts thereof.

The α-hydroxycarboxylic acid of general formula (I-d) can be produced by reacting the aldehyde of general formula (II) with a cyanide and then hydrolyzing the resulting α-hydroxynitrile of general formula

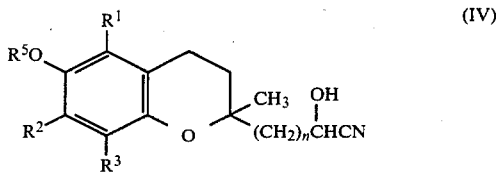
(IV)

wherein $R^1$, $R^2$, $R^3$, $R^5$ and n each have the same meanings as in general formula (II). Said cyanide includes hydrogen cyanide; an alkali metal cyanide such as sodium cyanide, potassium cyanide, etc.; an organic aluminum cyanide such as dimethylaluminum cyanide, diethylaluminum cyanide, etc.; and an organic silicon cyanide such as trimethylsilyl cyanide, dimethyl-tert-butylsilyl cyanide, etc. The reaction of the aldehyde of general formula (II) with such cyanide can be carried out under conditions which are generally known for cyanohydrin formation. The following are typical examples of the cyanohydrin formation reaction:

[REACTION EXAMPLE A]

Reaction of aldehyde with hydrogen cyanide

The aldehyde of general formula (II) is reacted with about 1–10 moles, preferably about 1–3 moles, per mole of aldehyde, of hydrogen cyanide, preferably in the presence of a catalytically small amount of an alkali metal cyanide such as sodium cyanide, potassium cyanide, etc. in the presence or absence of an inert solvent such as diethyl ether, methanol, ethanol, benzene, toluene, dichloroethane, chloroform, etc. with cooling or under pressure, whereby the α-hydroxynitrile of general formula (IV) is produced.

[REACTION EXAMPLE B]

Reaction of aldehyde with alkali metal cyanide

The aldehyde of general formula (II) is first reacted with about 1–2 moles, per mole of aldehyde, of an alkali metal bisulfite such as sodium bisulfite, potassium bisulfite, etc., for instance, in a mixed solvent composed of water and ethanol at about 0°–50° C. to give an aldehyde-alkali metal bisulfite adduct. The adduct in the reaction mixture is then reacted with about 1–2 moles, per mole of aldehyde, of an alkali metal cyanide at about 0°–5° C. to give the α-hydroxynitrile of general formula (IV).

[REACTION EXAMPLE C]

Reaction of aldehyde with organic aluminum cyanide or organic silicon cyanide

The aldehyde of general formula (II) is reacted with about 1–3 moles, preferably about 1–2 moles, per mole of aldehyde, of an organic aluminum cyanide or an organic silicon cyanide in an inert solvent such as methylene chloride, dichloroethane, carbon tetrachloride, tetrahydrofuran, benzene, toluene, etc. at about −50° C. to 50° C., preferably about −20° C. to room temperature to give the α-hydroxynitrile of general formula (IV).

The α-hydroxycarboxylic acid of general formula (I-d) can be produced by hydrolyzing, by the conventional method, the α-hydroxynitrile of general formula (IV) as obtained by the above cyanohydrin formation reaction. The hydrolysis can be performed, for example, at room temperature or under heating, in the presence of a mineral acid such as hydrochloric acid, sulfuric acid, etc. or an alkali metal hydroxide such as sodium hydroxide, potassium hydroxide, etc., if necessary in the presence of a high-boiling alcohol such as glycerol, ethylene glycol, methylcellosolve, etc.

The α-hydroxycarboxylic acid of general formula (I-d), when subjected to per se known general esterification or salt formation reaction, gives an ester or salt thereof. Thus, for instance, reacting the α-hydroxycarboxylic acid of general formula (I-d) with an equimolar amount to large excess of an alkyl alcohol such as methyl alcohol, ethyl alcohol, butyl alcohol, octyl alcohol, stearyl alcohol, etc. in the presence of an acid catalyst such as p-toluenesulfonic acid, sulfuric acid, strongly acidic ion exchange resin, etc. in the presence or absence of an inert solvent such as benzene, toluene, dichloroethane, etc. at a temperature of room temperature to the refluxing temperature, preferably while removing the by-product water out of the system, whereby the corresponding α-hydroxycarboxylic acid ester is obtained. When the α-hydroxycarboxylic acid of general formula (I-d) is reacted with an equimolar amount of an alkali metal hydroxide such as potassium hydroxide, sodium hydroxide, etc. or ammonia or an amine such as methylamine, dimethylamine, trimethylamine, triethylamine, tetramethylammoniun hydroxide, etc. in the presence of water and/or a lower alcohol such as methyl alcohol, ethyl alcohol, propyl alcohol, etc., the corresponding salt of said α-hydroxycarboxylic acid is obtained. The thus-obtained alkali metal salt of the α-hydroxycarboxylic acid is reacted with an alkaline earth metal halide such as calcium chloride, magnesium chloride, magnesium bromide, etc. in the presence of water and/or a lower alcohol such as methyl alcohol, ethyl alcohol, etc., whereby the corresponding alkaline earth metal salt of the α-hydroxycarboxylic acid is produced.

The α-hydroxycarboxylic acid of general formula (I-d) and an ester thereof as obtained by the above method can be separated and recovered by the conventional method. Thus, for example, water is added to the reaction mixture, followed as necessary by addition of an acid such as hydrochloric acid, sulfuric acid, etc. so as to make the mixture weakly acidic, and then the whole mixture is extracted with diethyl ether or the like. The extract is washed with water and then dried, the solvent is distilled off, and the residue is purified by recrystallization or column chromatography to give the α-hydroxycarboxylic acid of general formula (I-d) or an ester thereof. For separation and recovery of the salt of α-hydroxycarboxylic acid of general formula (I-d) from the reaction mixture, said reaction mixture is concentrated to dryness in the conventional manner.

When in the salt form, the α-amino acid of general formula (I-a) and an ester thereof as well as the α-hydroxycarboxylic acid of general formula (I-d) are fairly soluble, so that separation of the salts from fat-soluble impurities from the reaction process can be done with ease. The salts deprived of fat-soluble impurities can be converted to highly pure α-amino acids or α-hydroxycarboxylic acids by the conventional neutralization with an acid such as hydrochloric acid, sulfuric acid, etc. These α-amino acids or α-hydroxycarboxylic acids can further be converted to highly pure esters of said α-amino acids or α-hydroxycarboxylic acids by subjecting the acids to the conventional esterification.

The amino alcohol of general formula (I-b) can be produced by reducing the α-amino acid of general formula (I-a), for example, with about 1–3 moles, per mole of α-amino acid, of lithium aluminium hydride in a solvent such as tetrahydrofuran, etc. under refluxing. The amino alcohol of general formula (I-b), when subjected to per se known general esterification and/or salt formation reaction, gives an ester or salt of said amino alcohol, or a salt of the ester. The amino alcohol of general formula (I-b) and an ester thereof and their salts as thus obtained can be separated and recovered by the conventional method.

The amine of general formula (I-c) can be produced by reacting the aldehyde of general formula (II) with about 1–2 moles, per mole of aldehyde, of hydroxyamine in an aqueous alcohol such as methyl alcohol, ethyl alcohol, etc. at a temperature of 0° C. to room temperature and then reducing the thus-obtained oxime of general formula

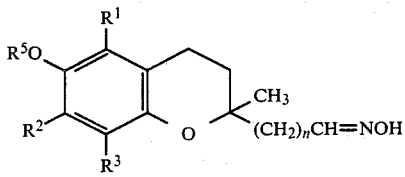

(V)

wherein $R^1$, $R^2$, $R^3$, $R^5$ and n each have the same meanings as in general formula (II), for example, with about 0.75–2 moles, per mole of oxime, of lithium aluminium hydride in a solvent such as tetrahydrofuran, etc. under refluxing. The amine of general formula (I-c), when subjected to per se known general salt formation reaction, gives a salt of said amine. The thus-obtained amine and a salt thereof can be separated and recovered by the conventional method.

The starting aldehydes of general formula (II) can be prepared easily by oxidizing alcohols of general formula (V) given below, which are known compounds, for example, with chromic anhydride in the presence of pyridine [cf. Helvetica Chimica Acta, 61, 837–843 (1978)].

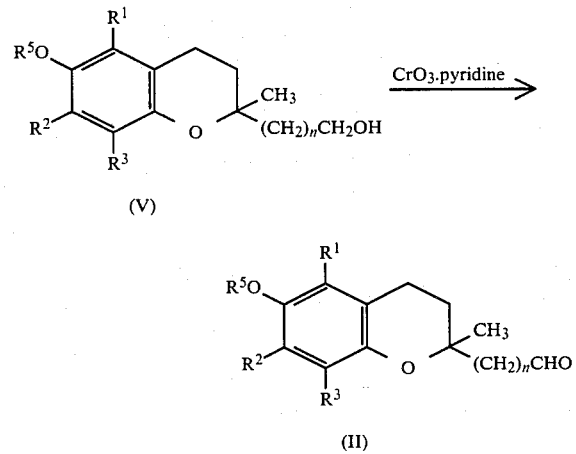

Among the chroman compounds (I), the chroman compounds (I-1) have potent antioxidant activity. The compounds in which R is a carboxyl group and $R^4$ is a protective group in general formula (I) can be converted to the above-mentioned antioxidant-active chroman compounds (I-1) by replacing the protective group with a hydrogen atom by the conventional method.

The chroman compounds (I-1) are used as antioxidants for organic materials sensitive to oxidative factors, such as oils and fats, waxes, pharmaceutical preparations, cosmetics and toiletries, rubber products, synthetic resins, processed foodstuffs, etc. by incorporating the same chroman compounds to said organic materials. These antioxidants are preferably incorporated into such organic materials as the oils and fats and foodstuffs containing unsaturated fatty acids (e.g. oleic acid, linoleic acid, linolenic acid, arachidonic acid, etc.) or esters thereof; and synthetic resins including polyolefins such as polyethylene, polypropylene, ethylene-propylene copolymer, etc.; diene polymers such as polybutadiene, polyisoprene, ethylene-propylenediene terpolymer, etc.; styrenic resins such as polystyrene, styrene-butadiene copolymer, styrene-acrylonitrile copolymer, methacrylate-styrene-acrylonitrile copolymer, ABS resin, etc.; halogen-containing resins such as polyvinyl chloride, polyvinylidene chloride, vinyl chloride-vinylidene chloride copolymer, polychloroprene, chlorinated polyethylene, etc.; polymers of α,β-unsaturated acids or derivatives thereof such as polyacrylates, polyacrylamide, polyacrylonitrile, etc.; polymers of unsaturated alcohols or acyl derivatives thereof such as polyvinyl alcohol, polyvinyl acetate, styrene-vinyl acetate copolymer, etc.; polyurethane; aliphatic or aromatic polyamides; polyimides, poly(amide-imide); polyacetal; polycarbonate; saturated or unsaturated polyesters; epoxy resins; phenolic resins; polyphenylene oxide; urea resin; melamine resin; etc. Among the chroman compounds (I-1), the salts are suitably used as antioxidants particularly for processed foodstuffs, taking advantage of their being water-soluble. While the amount of the antioxidant should vary with the required degree of stabilization effect sought in the organic material, it can be selected from the range of about 0.001 to 20 weight percent relative to the organic material. For the stabilization of a synthetic resin, the antioxidant can be used advantageously in an amount of from about 0.001 to 5 weight percent based on the resin and when the organic material is a highly sensitive material such as a vitamin, the amount of the antioxidant may be increased to about 20 weight percent.

The chroman compounds (I-1) are used either alone or in combination with one or more other antioxidants, particularly phenolic antioxidants such as pentaerythritol tetrakis[3-(3,5-di-tert-butyl-4-hydroxyphenyl)propionate], octadecyl 3-(3,5-di-tert-butyl-4-hydroxyphenyl)propionate, etc. These phenolic and other antioxidants are generally used in a proportion of about 10 to 500 weight percent relative to the chroman compounds (I-1). Further, the chroman compounds (I-1) can be used in combination with synergistic auxiliary stabilizers such as calcium stearate, distearyl thiodipropionate, etc. These auxiliary stabilizers are used in a proportion of about 50 to 500 weight percent relative to the chroman compounds (I-1).

Thus, the organic composition prepared by incorporating the chroman compounds (I-1) in an organic material is very stable against unfavorable effects due to oxidative factors. The term "unfavorable effects" as used herein means the degradation, decomposition, etc.

of organic materials. Taking synthetic resins as an example, the unfavorable effects include the decomposition and undesirable crosslinking of macromolecules, and other changes which manifest as aging, brittleness, discoloration, depression of softening point, etc.

Among the chroman compounds (I), the chroman compounds (I-2) show excellent analgesic activity. In addition, these compounds have low toxicity. For example, β-(2,3-dihydro-6-hydroxy-2,5,7,8-tetramethyl-2H-benzopyranyl) alanine hydrochloride has such low acute toxicity that $LD_{50}$ value (oral administration) is 2,624 g/kg for male mice. So, the chroman compounds (I-2) can be used as an analgesic.

Among the chroman compounds (I-2), the pharmaceutically acceptable esters of the compound in which R in general formula (I-2) is a hydroxymethyl group include such ester form as a lower fatty acid ester, e.g. acetic acid ester, propionic acid ester, etc.; a higher fatty acid ester, e.g. palmitic acid ester, oleic acid ester, etc.; a phosphoric acid ester, an ester of monomannosyl phosphate, etc. and the like. And the pharmaceutically acceptable esters of the compound in which R in general formula (I-2) is a carboxyl group include such ester form as an alkyl ester, e.g. methyl ester, ethyl ester, propyl ester, butyl ester, octyl ester, tetradecyl ester, stearyl ester, etc. The pharmaceutically acceptable salts of the compound of general formula (I-2) include such salt form as an alkali metal salt, e.g. lithium salt, sodium salt, potassium salt, etc; hydrochloride, nitrate, methanesulfonate and the like.

The compounds in which A is an amino group and $R^4$ is a protective group in general formula (I) can be converted to the above-mentioned analgesic-active chroman compound (I-2) by replacing the protective group with a hydrogen atom by the conventional method.

The pharmaceutical composition of the invention for analgesic can be formulated into various dosage forms by using means known per se. For example, the dosage forms may be those suitable for oral administration such as tablets, granules, powders, coated tablets, hard capsules, soft capsules and oral liquid preparations and those suitable for injection such as suspensions, liquid preparations, and oily or aqueous emulsions.

The pharmaceutical composition of the invention may contain various pharmaceutically acceptable liquid or solid diluents or carriers known per se. Examples of such diluents or carriers include syrup, gum arabic, gelatin, sorbitol, tragacanth, polyvinylpyrrolidone, magnesium stearate, talc, polyethylene glycol, silica, lactose, sucrose, corn starch, calcium phosphate, glycine, potato starch, calcium carboxymethylcellulose, sodium laurylsulfate, water, ethanol, glycerol, mannitol and phosphate buffer.

The pharmaceutical composition of the invention may further include adjuvants conventionally used in the field of pharmaceutical production, such as coloring agents, flavors, corrigents, antiseptics, dissolution aids, suspending agents and dispersing agents.

The pharmaceutical composition of the invention may be in the form filled in a large dosage container as well as in a fixed dosage form such as tablets, capsules, coated tablets, ampoules, etc. exemplified hereinabove.

The pharmaceutical composition of the invention contains an amount, effective for analgesic, of the compound of general formula (I-2) and its pharmaceutically acceptable ester and/or salt. Its dosage can be varied properly depending upon the condition of the subject, the purpose of administration, etc. For example, it is about 50 to about 2,000 mg, preferably about 100 to about 500 mg, per day for an adult.

The pharmaceutical composition of the invention can be administered through various routes, for example, orally or by injection (e.g., intravenous, subcutaneous, intramuscular). Oral administration and intravenous injection are especially preferred.

The following examples, test examples and formulation examples illustrate the invention in more detail. It is to be noted, however, that these examples, test examples and formulation examples are by no means limitative of the invention.

EXAMPLE 1

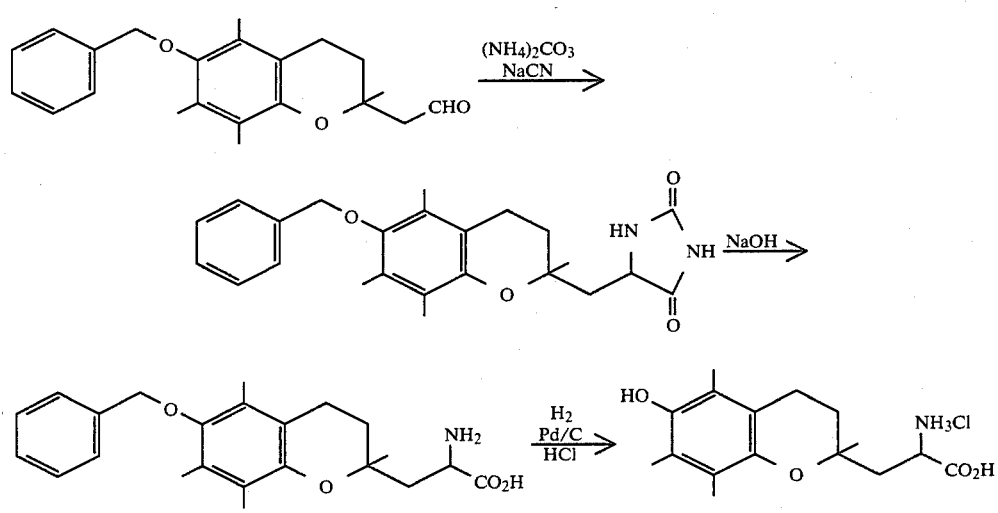

(1) To a solution of 3.38 g of 2-(6-benzyloxy-2,3-dihydro-2,5,7,8-tetramethyl-2H-benzopyranyl)acetaldehyde in 25 ml of ethanol, there were added 14 ml of water, 4.52 g of ammonium carbonate and 0.98 g of sodium cyanide, followed by heating at 50°–55° C. with stirring for 4 hours. The reaction mixture was concentrated under reduced pressure, 2 ml of concentrated hydrochloric acid was added to the residue, and the mixture was heated at 90° C. for 5 minutes. The reaction mixture was cooled, water was added, and the resulting precipitate was collected by filtration, washed with water and diethyl ether, and dried under reduced pressure to give 3.42 g (83.8% yield) of 5-[(6-benzyloxy-2,3-dihydro-2,5,7,8-tetramethyl-2H-benzopyranyl)methyl]imidazolidine-2,4-dione characterized by the following:

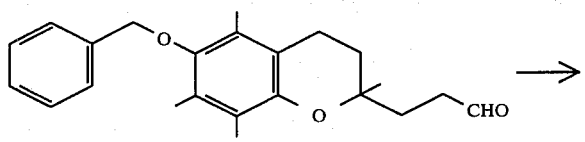

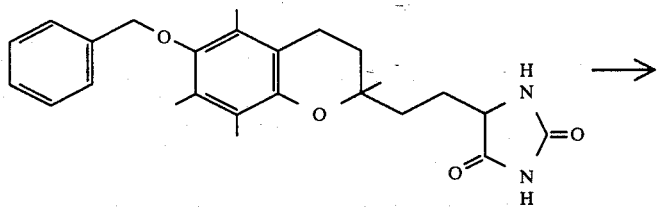

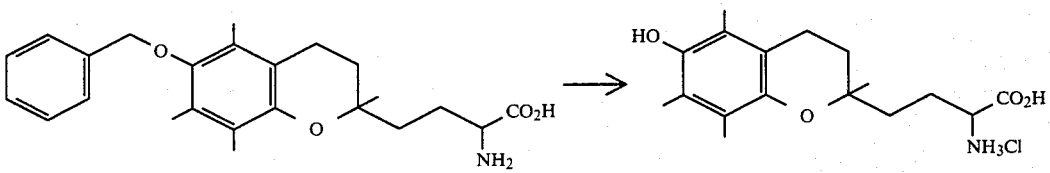

FD mass spectrum: [M]+ 408

NMR spectrum (90 MHz) $\delta_{DMSO-d6}^{HMS}$: 1.21 (s, 3H); 1.5–2.7 (m, 15H); 3.26 (s, 2H); 4.0–4.3 (m, 1H); 4.6 (s, 2H); 7.25–7.6 (m, 5H)

(2) A mixture of 3.15 g of 5-[(6-benzyloxy-2,3-dihydro-2,5,7,8-tetramethyl-2H-benzopyranyl)methyl]-imidazolidine-2,4-dione obtained by the above procedure (1), 1.6 g of sodium hydroxide and 30 ml of water was heated with stirring in a sealed tube at 120° C. for 15 hours. Water was then added to the reaction mixture, the insoluble matter was filtered off, the filtrate was washed with diethyl ether, and the aqueous layer was neutralized with diluted hydrochloric acid. The resulting precipitate was collected by filtration, washed with water and diethyl ether, and dried under reduced pressure to give 2.41 g (78.7% yield) of β-(6-benzyloxy-2,3-dihydro-2,5,7,8-tetramethyl-2H-benzopyranyl)alanine characterized by the following:

FD mass spectrum: [M]+ 383

NMR spectrum (90 MHz): $\delta_{DMSO-d6}^{HMS}$: 1.2 (s, 3H); 1.5–2.7 (m, 15H); 3.8–4.1 (m, 1H); 4.59 (s, 2H); 7.25–7.57 (m, 5H); 7.6–9.5 (br. s, 3H)

(3) β-(6-Benzyloxy-2,3-dihydro-2,5,7,8-tetramethyl-2H-benzopyranyl)alanine (2.30 g) obtained by the above procedure (2) was dissolved in 200 ml of ethanol, followed by addition of 12 ml of 1N hydrochloric acid and 2.0 g of 5% palladium-on-activated carbon. The mixture was stirred at room temperature in a hydrogen atmosphere for 2 days. The reaction mixture was filtered, water was added to the filtrate, and low boiling components were distilled off under reduced pressure. The residue was dissolved in ethanol, followed by recrystallization by addition of diethyl ether. There was thus obtained 1.21 g (61.2% yield) of crystalline β-(2,3-dihydro-6-hydroxy-2,5,7,8-tetramethyl-2H-benzopyranyl)alanine hydrochloride characterized by the following:

FD mass spectrum: [M-HCl]+ 293

NMR spectrum (90 MHz) $\delta_{DMSO-d6}^{HMS}$: 1.5 (s, 3H); 1.6–2.65 (m, 15H); 3.8–4.1 (m, 1H); 7.4 (br. s, 1H); 8.5 (br. s, 3H)

EXAMPLE 2

Using 3.52 g of 3-(6-benzyloxy-2,3-dihydro-2,5,7,8-tetramethyl-2H-benzopyranyl)propionaldehyde in place of 3.38 g of 2-(6-benzyloxy-2,3-dihydro-2,5,7,8-tetramethyl-2H-benzopyranyl)acetaldehyde, the procedure of Example 1-(1) was followed for reaction, separation and recovery. There was obtained 3.17 g (75.1% yield) of 5-[2-(6-benzyloxy-2,3-dihydro-2,5,7,8-tetramethyl-2H-benzopyranyl)ethyl]imidazolidine-2,4-dione characterized by the following:

FD mass spectrum: [M]+ 422

NMR spectrum (90 MHz) $\delta_{DMSO-d6}^{HMS}$: 1.13 (s, 3H); 1.3–2.7 (m, 17H); 3.3 (br.s, 2H); 3.85–4.1 (m, 1H); 4.57 (s, 2H); 7.25–7.6 (m, 5H)

The procedure for reaction, separation and recovery as described in Example 1-(2) was followed except that 3.26 g of 5-[2-(6-benzyloxy-2,3-dihydro-2,5,7,8-tetramethyl-2H-benzopyranyl)ethyl]imidazolidine-2,4-dione was used in place of 3.15 g of 5-[(6-benzyloxy-2,3-dihydro-2,5,7,8-tetramethyl-2H-benzopyranyl)methyl]-imidazolidine-2,4-dione. There was obtained 2.41 g (78.6% yield) of 2-amino-4-[2-(6-benzyloxy-2,3-dihydro-2,5,7,8-tetramethyl-2H-benzopyranyl)]butyric acid characterized by the following:

FD mass spectrum: [M]+ 397

NMR spectrum (90 MHz) $\delta hd CD_3OD^{HMS}$: 1.24, 1.28 (s, 3H); 1.6–2.8 (m, 17H); 4.1–4.45 (m, 1H); 4.68 (s, 2H); 4.73 (s, 3H); 7.2–7.5 (m, 5H)

The procedure for reaction, separation and recovery as described in Example 1-(3) was followed except that 2.38 g of 2-amino-4-[2-(6-benzyloxy-2,3-dihydro-2,5,7,8-tetramethyl-2H-benzopyranyl)]butyric acid was used in place of 2.30 g of β-(6-benzyloxy-2,3-dihydro-2,5,7,8-tetramethyl-2H-benzopyranyl)alanine. There was obtained 1.26 g (61.1% yield) of crystalline 2-amino-4-[2-(2,3-dihydro-6-hydroxy-2,5,7,8-tetramethyl-2H-benzopyranyl)]butyric acid hydrochloride characterized by the following:

FD mass spectrum: [M]+ 307

EXAMPLES 3–10

The procedure for reaction, separation and recovery as described in Example 1-(1) was followed using 10 millimoles of each aldehyde specifically given in Table 1 in place of 3.38 g (10 mmol) of 2-(6-benzyloxy-2,3-dihydro-2,5,7,8-tetramethyl-2H-benzopyranyl)-acetaldehyde, to give the corresponding hydantoin. The results thus obtained are shown in Table 1.

TABLE 1

| Example No. | Starting aldehyde | Hydantoin (Product) | Yield (%) | FD mass spectrum |
|---|---|---|---|---|
| 3 | | | 64 | $[M]^+$ 394 |
| 4 | | | 72 | $[M]^+$ 360 |
| 5 | | | 53 | $[M]^+$ 318 |
| 6 | | | 76 | $[M]^+$ 318 |
| 7 | | | 81 | $[M]^+$ 380 |

TABLE 1-continued
| Example No. | Starting aldehyde | Hydantoin | Yield (%) | FD mass spectrum |
|---|---|---|---|---|
| 8 | 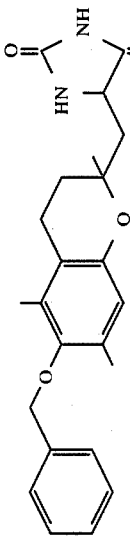 | 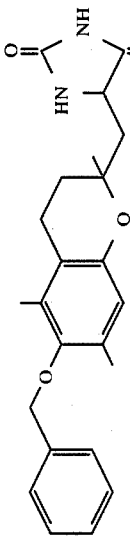 | 84 | [M]+ 394 |
| 9 | 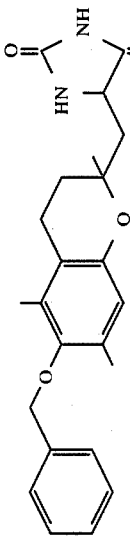 | 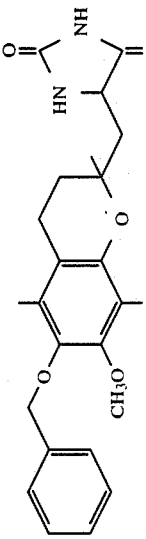 | 80 | [M]+ 440 |
| 10 | 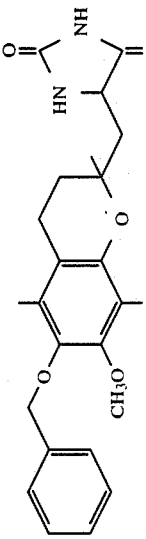 | 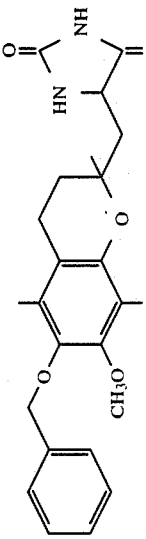 | 81 | [M]+ 430 |

The procedure for reaction, separation and recovery as described in Example 1-(2) was followed using 7.7 millimoles of each hydantoin specifically given in Table 2 as obtained by the same method as above in place of 3.15 g (7.7 mmol) of 5-[(6-benzyloxy-2,3-dihydro-2,5,7,8-tetramethyl-2H-benzopyranyl)methyl]-imidazolidine-2,4-dione, to give the corresponding α-amino acid. The results thus obtained are shown in Table 2.

TABLE 2

| Example No. | Starting hydantoin | α-Amino acid (Product) | Yield (%) | FD mass spectrum |
|---|---|---|---|---|
| 3 | [structure] | [structure] | 28 | [M]+ 369 |
| 4 | [structure] | [structure] | 57 | [M]+ 293 |
| 5 | [structure] | [structure] | 54 | [M]+ 293 |
| 6 | [structure] | [structure] | 52 | [M]+ 251 |
| 7 | [structure] | [structure] | 72 | [M]+ 355 |
| 8 | [structure] | [structure] | 81 | [M]+ 369 |
| 9 | [structure] | [structure] | 64 | [M]+ 415 |

| Example No. | Starting hydantoin | Product α-Amino acid | Yield (%) | FD mass spectrum |
|---|---|---|---|---|
| 10 | (structure) | (structure) | 78 | [M]+ 405 |

The procedure for reaction, separation and recovery as described in Example 1-(3) was followed using 6 millimoles of each α-amino acid specifically given in Table 3 as obtained by the same method as above in place of 2.30 g (6 mmol) of β-(6-benzyloxy-2,3-dihydro-2,5,7,8-tetramethyl-2H-benzopyranyl-alanine, to give the corresopnding α-amino acid hydrochloride. The results thus obtained are shown in Table 3.

TABLE 3

| Example No. | Starting α-amino acid | α-Amino acid hydrochloride | Yield (%) | FD mass spectrum |
|---|---|---|---|---|
| 3 | (chromanyl structure with OBn, CO₂H, NH₂) | (chromanyl structure with OH, CO₂H·HCl, NH₂) | 73 | [M−HCl]⁺ 279 |
| 7 | (chromanyl structure with OBn, NH₂, CO₂H) | (chromanyl structure with OH, NH₂, CO₂H·HCl) | 81 | [M−HCl]⁺ 265 |
| 8 | (chromanyl structure with OBn, NH₂, CO₂H) | (chromanyl structure with OH, NH₂, CO₂H·HCl) | 75 | [M−HCl]⁺ 279 |
| 9 | (dimethoxy chromanyl structure with OBn, NH₂, CO₂H) | (dimethoxy chromanyl structure with OH, NH₂, CO₂H·HCl) | 72 | [M−HCl]⁺ 325 |
| 10 | (naphtho-chromanyl structure with OBn, NH₂, CO₂H) | (naphtho-chromanyl structure with OH, NH₂, CO₂H·HCl) | 76 | [M−HCl]⁺ 315 |

EXAMPLE 11

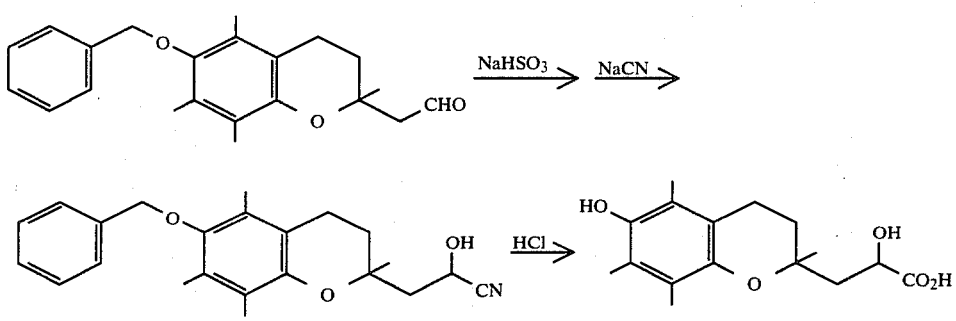

To a solution of 1.18 g of 2-(6-benzyloxy-3,4-dihydro-2,5,7,8-tetramethyl-2H-benzopyranyl)acetaldehyde in 13 ml of ethanol was added dropwise an aqueous solution (2 ml) of 0.73 g of sodium bisulfite. After precipitation of the sodium bisulfite adduct, an aqueous solution (1.5 ml) containing 0.34 g of sodium cyanide was added dropwise to the reaction mixture with vigorous stirring. After dropping, stirring was continued at room temperature for 4 hours, water was added to the reaction mixture, and extraction was performed with diethyl ether. The extract was washed with water and then low-boiling substances were distilled off. To the crude cyanohydrin thus obtained, there was added 20 ml of concentrated hydrochloric acid, followed by refluxing for an hour. After cooling, water was added to the reaction mixture, followed by extraction with diethyl ether. The extract was washed with water and dried over anhydrous magnesium sulfate, and low boiling substances were distilled off under reduced pressure. The concentrate obtained was dissolved in diethyl ether, and recrystallization was effected by adding n-hexane. There was thus obtained 0.84 g (81.9% yield) of 2-hydroxy-3-[2-(3,4-dihydro-6-hydroxy-2,5,7,8-tetramethyl-2H-benzopyranyl)]propionic acid characterized by the following:

FD mass spectrum: [M]+ 294
NMR spectrum (90 MHz): $\delta_{CDCl_3}^{HMS}$: 1.28 (s, 3H); 1.7–2.3 (m, 13H); 2.57 (t, J=7 Hz, 2H); 4.33–4.57 (m, 1H); 6.3 (br. s, 3H)

EXAMPLE 12

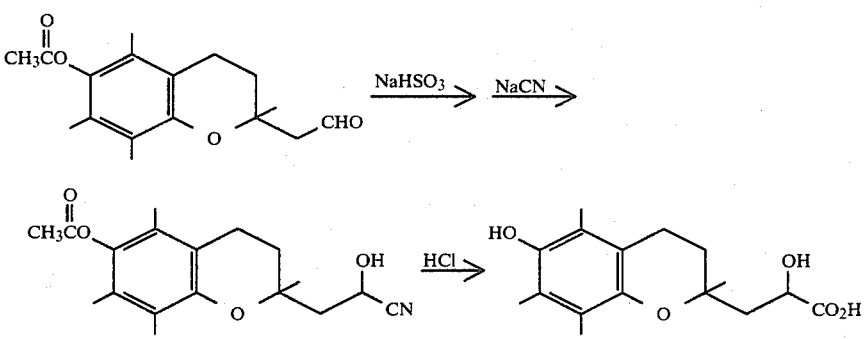

The procedure for reaction, separation and recovery as described in Example 11 was followed using 1.01 g of 2-(6-acetoxy-3,4-dihydro-2,5,7,8-tetramethyl-2H-benzopyranyl)acetaldehyde in place of 1.18 g of 2-(6-benzyloxy-3,4-dihydro-2,5,7,8-tetramethyl-2H-benzopyranyl)acetaldehyde used in Example 11. There was obtained 0.89 g (86.7% yield) of 2-hydroxy-3-[2-(3,4-dihydro-6-hydroxy-2,5,7,8-tetramethyl-2H-benzopyranyl)]-propionic acid.

EXAMPLES 13 AND 14

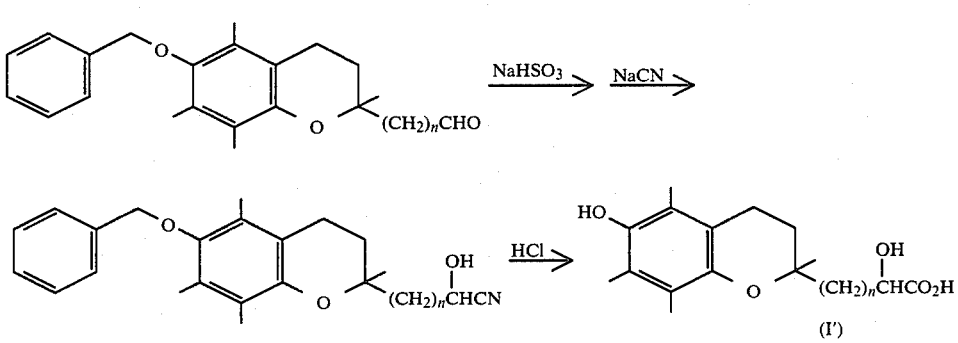

The procedure for reaction, separation and recovery as described in Example 11 was followed except that 1.13 g of 2-(6-benzyloxy-3,4-dihydro-2,5,7,8-tetramethyl-2H-benzopyranyl)carbaldehyde or 1.23 g of 3-(6-benzyloxy-3,4-dihydro-2,5,7,8-tetramethyl-2H-benzopyran-2-yl) propionic aldehyde was used in place of 1.18 g of 2-(6-benzyloxy-3,4-dihydro-2,5,7,8-tetramethyl-2H-benzopyranyl)acetaldehyde used in Example 11, to give the corresponding 2-hydroxy-2-[2-(3,4-dihydro-6-hydroxy-2,5,7,8-tetramethyl-2H-benzopyranyl)]acetic acid or 2-hydroxy-4-[2-(3,4-dihydro-6-hydroxy-2,5,7,8-tetramethyl-2H-benzopyranyl)]butyric acid, respectively. The results obtained are shown in Table 4.

TABLE 4

| | | α-Hydroxycarboxylic acid (I') | |
|---|---|---|---|
| Example No. | n | Yield (%) | FD mass spectrum | NMR spectrum (90 MHz) $\delta_{CDCl}^{HMS}$ |
| 13 | 0 | 72.2 | [M]+ 280 | 1.23(s,3H); 1.7~2.3(m,11H); 2.6(t,J = 7Hz,2H); 4.12,4.13(s,1H); 6.5(br.s,3H) |
| 14 | 2 | 87.5 | [M]+ 308 | 1.17(s,3H); 1.5~2.2(m,15H); 2.55(t,J = 7 Hz,2H); 4.0~4.2(m,1H); 6.2(br.s,3H) |

EXAMPLES 15 and 16

The procedure for reaction, separation and recovery as described in Example 11 was followed using 1.29 g of 2-(6-benzyloxy-3,4-dihydro-7,8-dimethoxy-2,5-dimethyl-2H-benzopyranyl)acetaldehyde or 1.26 g of 2-(6-benzyloxy-3,4-dihydro-2,5-dimethyl-2H-naphthopyranyl)acetaldehyde in place of 1.18 g of 2-(6-benzyloxy-3,4-dihydro-2,5,7,8-tetramethyl-2H-benzopyranyl)acetaldehyde used in Example 11, to give the corresponding 2-hydroxy-3-[2-(3,4-dihydro-7,8-dimethoxy-2,5-dimethyl-6-hydroxy-2H-benzopyranyl)]propionic acid or 2-hydroxy-3-[2-[3,4-dihydro-6-hydroxy-2,5-dimethyl-2H-naphtho[1,2-b]-pyranyl]]propionic acid, respectively. The results obtained are shown in Table 5.

TABLE 5

| | α-Hydroxycarboxylic acid | | |
|---|---|---|---|
| Example No. | Product | Yield (%) | FD mass spectrum |
| 15 | (structure) | 61 | [M]+ 326 |
| 16 | (structure) | 73 | [M]+ 316 |

EXAMPLE 17

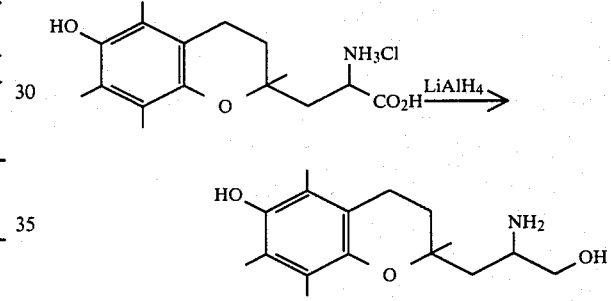

To a mixture of 0.36 g of lithium aluminium hydride and 30 ml of tetrahydrofuran was added by portions 2-(2,3-dihydro-6-hydroxy-2,5,7,8-tetramethyl-2H-benzopyranyl)alanine hydrochloride under refluxing. The reaction mixture was poured into a small amount of water, acidified with hydrochloric acid, and washed by diethyl ether. The aqueous layer was concentrated under reduced pressure and the residue was extracted with ethanol. The ethanol extract was basified with aqueous sodium bicarbonate and concentrated under reduced pressure. The resultant residue was extracted with dichloromethane and the extract was dried and evaporated under reduced pressure to give 1.05 g of 2-amino-3-[2-(2,3-dihydro-6-hydroxy-2,5,7,8-tetramethyl-2H-benzopyranyl)]-1-propanol characterized by the following:

FD mass spectrum: [M]+ 279

NMR spectrum (90 MHz) $\delta_{D_2O}^{HMS}$: 1.36 (s, 3H); 1.8–2.2 (m, 4H); 2.15, 2.17, 2.22 (each s, 9H); 2.6–2.9 (m, 2H); 3.7–4.1 (m, 3H)

EXAMPLE 18

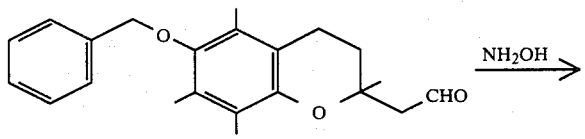

-continued

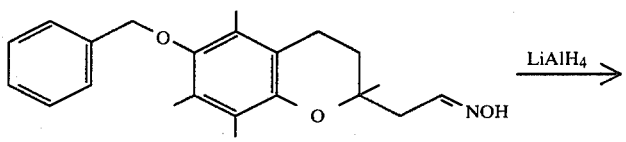

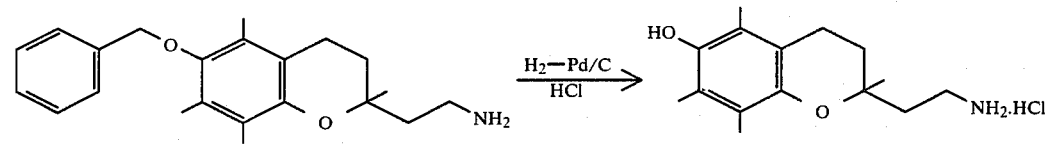

(1) To a mixture of 3.31 g of hydroxyamine hydrochloride in 3 ml of water, 2.59 g of sodium carbonate in 6 ml of water and 50 ml of ethanol, there was added 15.7 g of 2-(6-benzyloxy-2,3-dihydro-2,5,7,8-tetramethyl-2H-benzopyranyl)acetaldehyde in 100 ml of ethanol on ice bath, and the resulting mixture was stirred at room temperature overnight. Saturated aqueous solution of sodium chloride was added to the reaction mixture, and the resulting mixture was extracted with diethyl ether. The ether extract was dried with anhydrous sodium sulfate and evaporated to give 16.0 g of 2-(6-benzyloxy-2,3-dihydro-2,5,7,8-tetramethyl-2H-benzopyranyl)acetaldoxime.

(2) A solution of 15.0 g of 2-(6-benzyloxy-2,3-dihydro-2,5,7,8-tetramethyl-2H-benzopyranyl)acetaldoxime obtained by the above procedure (1) in 100 ml of tetrahydrofuran was added to a mixture of 2.42 g of lithium aluminium hydride and 100 ml of tetrahydrofuran under refluxing. After the reaction was completed, the reaction mixture was poured into ice-water, acidified with hydrochloric acid, and extracted with dichloromethane. The extract was dried and evaporated under reduced pressure. Aqueous solution of sodium hydroxide was added to the resultant residue, and the resulting mixture was extracted with diethyl ether. The ether extract was dried and evaporated to give 2-(6-benzyloxy-2,3-dihydro-2,5,7,8-tetramethyl-2H-benzopyranyl)ethylamine characterized by the following:

FD mass spectrum: [M]+ 339

NMR spectrum (90 MHz) $\delta_{CDCl_3}^{HMS}$: 1.17 (s, 3H); 1.5-2.0 (m, 4H); 1.92 (s, 3H); 2.07 (s, 3H); 2.14 (s, 3H); 2.3-2.6 (m, 2H); 4.0-4.4 (m, 2H); 4.62 (s, 2H); 7.2-7.5 (m, 5H)

(3) A mixture of 2-(6-benzyloxy-2,3-dihydro-2,5,7,8-tetramethyl-2H-benzopyranyl)ethylamine obtained by the above procedure (2), 1.0 g of 5% palladium-on-activated carbon, 20 ml of 2N hydrochloric acid and 100 ml of ethanol was stirred at room temperature overnight under hydrogen atmosphere. After the reaction was completed, the reaction mixture was filtered and the filtrate was concentrated under reduced pressure. The residue was dissolved in ethanol, and precipitated by addition of n-hexane. The precipitate was collected by filtration, washed with n-hexane and dried to give 8.6 g of 2-(2,3-dihydro-6-hydroxy-2,5,7,8-tetramethyl-2H-benzopyranyl) ethylamine hydrochloride characterized by the following:

FD mass spectrum: [M - HCl]+ 249

NMR spectrum (90 MHz) $\delta_{D_2O}^{HMS}$: 1.24 (s, 3H); 1.6-2.0 (m, 4H); 2.03, 2.06, 2.09 (each s, 9H); 2.4-2.8 (m, 2H); 2.8-3.2 (m, 2H)

EXAMPLE 19

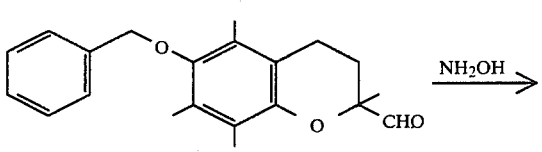

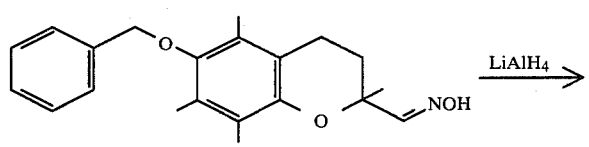

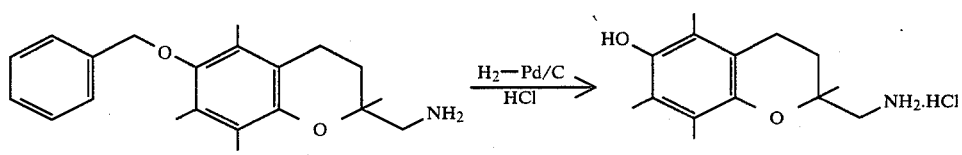

(1) To a mixture of 3.31 g of hydroxyamine hydrochloride in 3 ml of water, 2.59 g of sodium carbonate in 6 ml of water and 50 ml of ethanol, there was added 15 g of 2-(6-benzyloxy-2,3-dihydro-2,5,7,8-tetramethyl-2H-benzopyranyl)carbaldehyde in 100 ml of ethanol on ice bath, and the resulting mixture was vigorously stirred at room temperature overnight. Saturated aqueous solution of sodium chloride was added to the reaction mixture, and the resulting mixture was extracted with diethyl ether. The extract was dried with anhydrous sodium sulfate and evaporated, and the residue was purified by silica gel column chromatography to give 14 g of 2-(6-benzyloxy-2,3-dihydro-2,5,7,8-tetramethyl-2H-benzopyranyl)carbaldoxime.

(2) A solution of 14 g of 2-(6-benzyloxy-2,3-dihydro-2,5,7,8-tetramethyl-2H-benzopyranyl)carbaldoxime obtained by the above procedure (1) in 100 ml of tetrahydrofuran was added to a mixture of 2.4 g of lithium aluminium hydride and 100 ml of tetrahydrofuran under refluxing. After the reaction was completed, the reaction mixture was poured into ice-water, acidified with hydrochloric acid, and extracted with dichloromethane. The extract was dried and evaporated under reduced pressure. Aqueous solution of sodium hydroxide was added to the resultant residue, and the resulting mixture was extracted with diethyl ether. The ether extract was dried, and hydrogen chloride was bubbled into the extract. After evaporation under reduced pressure, the resultant residue was dissolved in dichloromethane and precipitated by addition of n-hexane. The precipitate was collected by filtration and dried to give 7.0 g of 2-(6-benzyloxy-2,3-dihydro-2,5,7,8-tetramethyl-2H-benzopyranyl)methylamine hydrochloride characterized by the following:

FD mass spectrum: $[M - HCl]^+$ 325

NMR spectrum (90 MHz) $\delta_{DMSO\text{-}d6}^{HMS}$: 1.24 (s, 3H); 1.7–2.0 (m, 2H); 2.05, 2.09, 2.12 (each s, 9H); 2.4–2.7 (m, 2H); 2.8–3.1 (m, 2H); 4.61 (s, 2H); 7.3–7.6 (m, 5H)

(3) A mixture of 7.0 g of 2-(6-benzyloxy-2,3-dihydro-2,5,7,8-tetramethyl-2H-benzopyranyl)methylamine hydrochloride obtained by the above procedure (2), 1.0 g of 5% palladium-on-activated carbon, 20 ml of 2N hydrochloric acid and 100 ml of ethanol was stirred at room temperature overnight under hydrogen atmosphere. After the reaction was completed, the reaction mixture was filtered and the filtrate was concentrated under reduced pressure. The residue was dissolved in ethanol, and precipitated by addition of n-hexane. The precipitate was collected by filtration and dried to give 4.3 g of (2,3-dihydro-6-hydroxy-2,5,7,8-tetramethyl-2H-benzopyranyl)methylamine hydrochloride characterized by the following:

FD mass spectrum: $[M - HCl]^+$ 235

NMR spectrum (90 MHz) $\delta_{DMSO\text{-}d6}^{HMS}$: 1.27 (s, 3H); 1.6–1.9 (m, 2H); 2.01 (s, 6H); 2.03 (s, 3H); 2.4–2.6 (m, 2H); 2.8–3.1 (m, 2H)

TEST EXAMPLES 1–16

Inhibition of linoleic acid oxidation

A test solution (10 ml) was prepared by adding each test compound, in an amount of 0.2% by weight on the linoleic acid basis, to a borate buffer (pH 9) containing $10^{-2}$M sodium linoleate. A 0.2 ml portion of the test solution was heated at 70° C. for a specified period of time. After heating, 4.7 ml of 75% ethanol and 0.1 ml of 30% ammonium thiocyanate were added to said test solution, and the mixture was stirred well. Then, 0.1 ml of a ferrous chloride solution [the supernatant obtained by adding an aqueous ferrous sulfate solution (0.6 g/50 ml) and 10 ml of concentrated hydrochloric acid to an aqueous barium chloride solution (0.5 g/50 ml), followed by adequate stirring and standing for a while] was added to said mixture. Exactly 3 minutes later, the resulting solution was measured for the absorbance at 500 m$\mu$. In this way, the trivalent iron formed by the oxidative action of sodium linoleate peroxides was assayed and, based on the assay data, the test compounds were compared with respect to antioxidant activity [cf. Shokuhin Kogaku Jikkensho (Experiments in Food Engineering), vol. I, edited by the Department of Food Engineering, Faculty of Agriculture, Kyoto University, pages 634–635]. The greater the absorbance of the test solution after heating is, the greater the amount of sodium linoleate peroxides formed is. The results obtained in the above manner are shown in Table 6.

TABLE 6

| Test Example No. | Test compound | Test solution (No heating) | Absorbance Solution after 1 hr. of heating | Solution after 2 hrs. of heating | Solution after 3 hrs. of heating |
|---|---|---|---|---|---|
| 1 | Blank | 0.03 | 0.09 | 0.23 | 0.29 |
| 2 | α-Tocopherol* | — | 0.07 | 0.19 | 0.30 |
| 3 | Ascorbic acid | — | 0.10 | 0.21 | 0.30 |
| 4 | Sodium erithorbate | — | 0.11 | 0.17 | 0.18 |
| 5 | [structure] | — | 0.02 | 0.03 | 0.03 |
| 6 | [structure] | — | 0.02 | 0.03 | 0.03 |
| 7 | [structure] | — | 0.02 | 0.03 | 0.04 |

TABLE 6-continued
| Test Example No. | Test compound | Absorbance | | | |
|---|---|---|---|---|---|
| | | Test solution (No heating) | Solution after 1 hr. of heating | Solution after 2 hrs. of heating | Solution after 3 hrs. of heating |
| 8 | 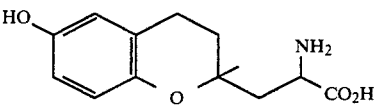 | — | 0.02 | 0.03 | 0.03 |
| 9 | 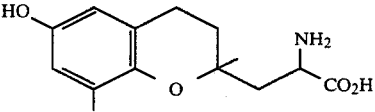 | — | 0.02 | 0.03 | 0.03 |
| 10 | 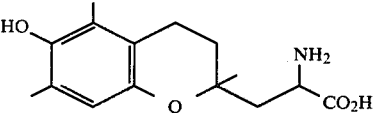 | — | 0.02 | 0.03 | 0.04 |
| 11 | 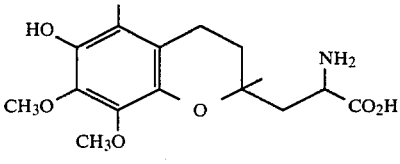 | — | 0.02 | 0.03 | 0.05 |
| 12 | 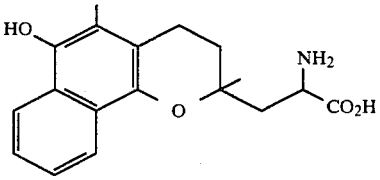 | — | 0.02 | 0.03 | 0.05 |
| 13 | 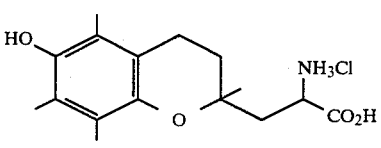 | — | 0.02 | 0.03 | 0.04 |
| 14 | 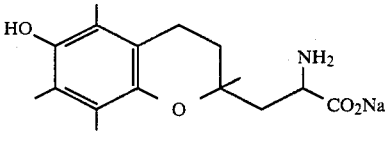 | — | 0.02 | 0.03 | 0.03 |
| 15 | 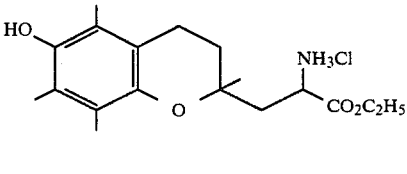 | — | 0.02 | 0.03 | 0.05 |
| 16 | 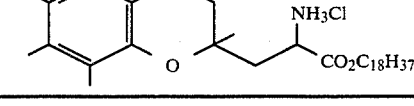 | — | 0.03 | 0.04 | 0.07 |
*For dissolution, an equal amount of a commercial nonionic surfactant "Tween 20" was added.

TEST EXAMPLES 17–28

To each 100 g of ethyl linoleate was added 0.020 g of one of the test compounds indicated in Table 7 to prepare a test solution. A 20 ml portion of each test solution was exposed to the accelerated conditions of aeration of 2.33 cc/sec. at 97.8° C. in an AOM (Antioxygen Method) test and the time period till the POV (peroxide value) reached 100 meq/kg was determined. The results are presented in Table 7.

TABLE 7

| Test Example No. | Test compound | Time (hrs.) till POV = 100 meq/kg |
|---|---|---|
| 17 | No addition | 0.2 |
| 18 | α-Tocopherol | 1.4 |
| 19 | (structure) | 2.3 |
| 20 | (structure) | 2.4 |
| 21 | (structure) | 2.0 |
| 22 | (structure) | 2.1 |
| 23 | (structure) | 2.3 |
| 24 | (structure) | 2.1 |
| 25 | (structure) | 2.2 |
| 26 | (structure) | 2.3 |
| 27 | (structure) | 2.2 |
| 28 | (structure) | 1.9 |

TEST EXAMPLE 29

Pharmacological tests

β-(2,3-Dihydro-6-hydroxy-2,5,7,8-tetramethyl-2H-benzopyranyl)alanine hydrochloride was evaluated for analgesic activity in the writhing test [cf. Koster et al., Fed. Proc., 18, 412 (1959)], local anesthetic activity in the tail pinch test [cf. Bianchi, C., Brit. J. Pharmacol., 11, 104 (1956)] and bronchodilator activity in lung perfusion [cf. Luduena, F. P., Arch. Int. Pharmacodyn., 111, 392 (1957)]. The results are shown in Table 8.

β-(2,3-Dihydro-6-hydroxy-2,5,7,8-tetramethyl-2H-benzopyranyl)alanine hydrochloride is active in the test for analgesic activity causing 84% inhibition of writhing, and also demonstrated a local anesthetic activity. An inhibition of isoprenaline-induced bronchodilation is also observed.

TABLE 8

| Test | Species | Route | Dose | Criterion for activity | Remarks | Activity observed |
|---|---|---|---|---|---|---|
| Analgesic-writhing | Rat | i.p. | 100 mg/kg | Score <50% of control group | Test 0.75 hr post-dose | 16% |
| Bronchodilator-lung perfusion | Guinea pig | In vitro | 300 μg as a single dose | >40% reduction in perfusion pressure | | Inhibited isoprenaline-induced bronchodilation: + |
| Local anesthetic | Mouse | s.c. | 3% | >3/5 protected | Tested at 15 min post-dose | 5/5 |

TEST EXAMPLES 30-33

Analgesic activity testing

β-(2,3-Dihydro-6-hydroxy-2,5,7,8-tetramethyl-2H-benzopyranyl)alanine hydrochloride [referred to as "Compound (1)"], 2-(2,3-dihydro-6-hydroxy-2,5,7,8-tetramethyl-2H-benzopyranyl)methylamine hydrochloride [referred to as "Compound (2)"], 2-amino-3-[2-(2,3-dihydro-6-hydroxy-2,5,7,8-tetramethyl-2H-benzopyranyl)]-1-propanol [referred to as "Compound (3)"] and Aspirin were evaluated for analgesic activity.

Male ddY strain mice in groups of ten each were used for the evaluation of analgesic activity by acetic acid writhing test [Koster et al., Federation Proc., 18, 412 (1959)]. The results are shown in Table 9.

TABLE 9

| Test Example No. | Test compound | dose (mg/kg, s.c.) | inhibition (%) |
|---|---|---|---|
| 30 | Aspirin | 100 | 40.8 |
| 31 | Compound (1) | 100 | 96.1 |
| 32 | Compound (2) | 100 | 65.6 |
| 33 | Compound (3) | 100 | 83.7 |

Specific examples of formulating the analgesic of the invention are shown below. It should be understood, however, that these examples are not limitative.

FORMULATION EXAMPLE 1

Injectable preparation:

Compound (1) (100 mg) was dissolved in 3 ml of physiological saline and put aseptically in a 3 ml. ampoule. The ampoule was sealed up by melting and heat sterilized to form an injectable preparation which was aseptic and did not contain a pyrogenetic substance.

FORMULATION EXAMPLE 2

Tablets:

| | |
|---|---|
| Compound (1) | 100 mg |
| Corn starch | 145 mg |
| Calcium carboxymethylcellulose | 40 mg |
| Polyvinylpyrrolidone | 9 mg |
| Magnesium stearate | 6 mg |

The above ingredients were mixed and directly tableted by a tableting machine to form tablets each weighing 300 mg.

What is claimed is:

1. A compound of general formula where A is an amino or hydroxyl group, R is a hydrogen atom or a hydroxymethyl or carboxyl group when A is an amino group, or a carboxyl group when A is a hydroxyl group, $R^1$ is a hydrogen atom or a lower alkyl group, $R^2$ and $R^3$ are the same or different and each is a hydrogen atom or a lower alkyl or alkoxy group or $R^2$ and $R^3$ combinedly represent a —CH=CH—CH=CH— group, $R^4$ is a hydrogen atom, a carboxylic acyl group, an alkyl group having 1 to 4 carbon atoms, a triphenylmethyl group, a benzyl group or a trimethylsilyl group, and n is an integer of 0-2, or pharmaceutically acceptable salts thereof, or when R is a carboxyl group, the pharmaceutically acceptable esters thereof.

2. The compound of claim 1, which is a compound of general formula wherein A is an amino or hydroxyl group, R is a hydrogen atom or a hydroxymethyl or carboxyl group when a is an amino group, or a carboxyl group when A is a hydroxyl group, $R^1$ is a hydrogen atom or a lower alkyl group, $R^2$ and $R^3$ are the same or different and each is a hydrogen atom or a lower alkyl or alkoxy group or $R^2$ and $R^3$ combinedly represent a —CH=CH—CH=CH— group and n is an integer or 0-2, or pharmaceutically acceptable salts thereof, or when R is a carboxyl group, the pharmaceutically acceptable esters thereof.

3. The compound of claim 2, wherein $R^1$, $R^2$ and $R^3$ in general formula each are a methyl group.

4. The compound of claim 3, which is β-(2,3-dihydro-6-hydroxy-2,5,7,8-tetramethyl-2H-benzopyranyl)alanine or a salt thereof.

5. The compound of claim 3, which is 2-amino-4-[2-(2,3-dihydro-6-hydroxy-2,5,7,8-tetramethyl-2H-benzopyranyl)]butyric acid or a salt thereof.

6. The compound of claim 3, which is 2-hydroxy-3-[2-(3,4-dihydro-6-hydroxy-2,5,7,8-tetramethyl-2H-benzopyranyl)]propionic acid or a salt thereof.

7. The compound of claim 3, which is 2-hydroxy-2-[2-(3,4-dihydro-6-hydroxy-2,5,7,8-tetramethyl-2H-benzopyranyl)]acetic acid or a salt thereof.

8. The compound of claim 3, which is 2-hydroxy-4-[2-(3,4-dihydro-6-hydroxy-2,5,7,8-tetramethyl-2H-benzopyranyl)]butyric acid or a salt thereof.

9. The compound of claim 3, which is 2-amino-3-[2-(2,3-dihydro-6-hydroxy-2,5,7,8-tetramethyl-2H-benzopyranyl)]-1-propanol or a salt thereof.

10. The compound of claim 3, which is 2-(2,3-dihydro-6-hydroxy-2,5,7,8-tetramethyl-2H-benzopyranyl)ethylamine or a salt thereof.

11. The compound of claim 3, which is 2-(2,3-dihydro-6-hydroxy-2,5,7,8-tetramethyl-2H-benzopyranyl)methylamine or a salt thereof.

12. The compound of claim 1, wherein A in the general formula is an amino group.

13. The compound of claim 1, wherein A in the general formula is a hydroxyl group.

* * * * *

UNITED STATES PATENT AND TRADEMARK OFFICE
CERTIFICATE OF CORRECTION

PATENT NO.  :  4,694,090

DATED       :  September 15, 1987

INVENTOR(S) :  Manzo SHIONO, et al.

It is certified that error appears in the above-identified patent and that said Letters Patent is hereby corrected as shown below:

Title page, Item (54) and

Column 1, line 3, where "ANALGERICS" should read --ANALGESICS--; column 2, line 52, where "carboxWnylic" should read --carboxylic--; column 4, line 19, where "mode" should read --mole--; column 7, lines 19-20, where "hydroxyamine" should read --hydroxylamine--; column 13, line 1, where "$[M]^+$" should read --$[M-HCl]^+$--; column 29, line 16, where "hydroxyamine" should read --hydroxylamine--; column 30, line 59, where "hydroxyamine" should read --hydroxylamine--; and columns 31-32, TABLE 6, Test Example No. 4, where "erithorbate" should read --erythorbate--.

Signed and Sealed this

Fifth Day of December, 1989

Attest:

JEFFREY M. SAMUELS

Attesting Officer    Acting Commissioner of Patents and Trademarks